United States Patent
Smith, III et al.

(10) Patent No.: US 9,670,122 B2
(45) Date of Patent: Jun. 6, 2017

(54) HYDROFORMYLATION PROCESS

(71) Applicant: Dow Technology Investments LLC, Midland, MI (US)

(72) Inventors: Cloid R. Smith, III, Charleston, WV (US); Morteza Mokhtarzadeh, Charleston, WV (US); Irvin B. Cox, St. Albans, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/910,268

(22) PCT Filed: Sep. 9, 2014

(86) PCT No.: PCT/US2014/054776
§ 371 (c)(1),
(2) Date: Feb. 5, 2016

(87) PCT Pub. No.: WO2015/047723
PCT Pub. Date: Apr. 2, 2015

(65) Prior Publication Data
US 2016/0194265 A1    Jul. 7, 2016

Related U.S. Application Data

(60) Provisional application No. 61/882,868, filed on Sep. 26, 2013.

(51) Int. Cl.
C07C 45/50 (2006.01)
B01J 19/00 (2006.01)
B01J 19/24 (2006.01)

(52) U.S. Cl.
CPC .......... *C07C 45/50* (2013.01); *B01J 19/0013* (2013.01); *B01J 19/2465* (2013.01); *B01J 2219/002* (2013.01); *B01J 2219/0006* (2013.01); *B01J 2219/0011* (2013.01); *B01J 2219/00063* (2013.01); *B01J 2219/00083* (2013.01); *B01J 2219/00094* (2013.01); *B01J 2219/00103* (2013.01); *B01J 2219/00114* (2013.01); *B01J 2219/00164* (2013.01); *B01J 2219/00204* (2013.01); *B01J 2219/00211* (2013.01); *B01J 2219/00213* (2013.01); *B01J 2219/00231* (2013.01)

(58) Field of Classification Search
CPC ..................................... C07C 45/50
USPC ....................................... 568/454
See application file for complete search history.

(56) References Cited

U.S. PATENT DOCUMENTS

| 3,527,809 A | 9/1970 | Pruett et al. |
| 4,148,830 A * | 4/1979 | Pruett ............ C07C 45/50 568/454 |
| 4,247,486 A | 1/1981 | Brewester et al. |
| 4,277,627 A * | 7/1981 | Bryant ............ C07C 45/50 568/454 |
| 4,329,507 A | 5/1982 | Takeda et al. |
| 4,518,809 A | 5/1985 | Forster et al. |
| 4,523,036 A | 6/1985 | Cornils et al. |
| 4,528,403 A | 7/1985 | Tano et al. |
| 4,717,775 A | 1/1988 | Billig et al. |
| 4,769,498 A | 9/1988 | Billig et al. |
| 5,237,106 A | 8/1993 | Babin et al. |
| 5,288,918 A | 2/1994 | Maher et al. |
| 5,312,996 A | 5/1994 | Packett |
| 5,360,938 A | 11/1994 | Babin et al. |
| 5,362,917 A | 11/1994 | Ogawa et al. |
| 5,367,106 A | 11/1994 | Unruh et al. |
| 5,491,266 A | 2/1996 | Babin et al. |
| 5,731,472 A | 3/1998 | Leung et al. |
| 5,741,944 A | 4/1998 | Bryant et al. |
| 5,741,945 A | 4/1998 | Bryant et al. |
| 5,744,650 A * | 4/1998 | Nicholson ............ B01J 19/18 568/454 |
| 5,763,679 A | 6/1998 | Nicholson et al. |
| 5,767,321 A | 6/1998 | Billig et al. |
| 5,929,289 A | 7/1999 | Abatjoglou et al. |
| 6,660,814 B1 | 12/2003 | Kroner et al. |
| 7,446,231 B2 | 11/2008 | Peterson et al. |
| 7,863,487 B2 | 1/2011 | Eisenschmid et al. |
| 7,906,688 B2 | 3/2011 | Brammer et al. |
| 8,389,774 B2 | 3/2013 | Becker et al. |
| 9,067,876 B2 * | 6/2015 | Becker ............ B01J 19/006 |
| 2005/0119509 A1 * | 6/2005 | Richter ............ C07C 45/50 568/454 |
| 2010/0006980 A1 | 1/2010 | Yoshinaga |

FOREIGN PATENT DOCUMENTS

| WO | 2012/008717 A2 | 1/2012 |
| WO | 2012/014541 A1 | 2/2012 |
| WO | 2013/095766 A1 | 6/2013 |

OTHER PUBLICATIONS

J. Falbe (ed) "New Syntheses with Carbon Monoxide" (Springer-Verlag, NY 1980) Section 1.2.4. pp. 18-21.
Van Elk, E.P. et al; Modelling of gas-liquid reactors—stability and dynamic behaviour of a hydroformylation reactor, infuence of mass transfer in the kinetics controlled regime. Chemical Engineering Science 56 (2001) 1491-1500).
PCT/US2014/054776, International Search Report and Written Opinion with a mailing date of Dec. 5, 2014.
PCT/US2014/054776, Second Written Opinion with a mailing date of Aug. 28, 2015.
PCT/US2014/054776, International Preliminary Report on Patentability with a mailing date of Dec. 16, 2015.
PCT/US2014/054776, Response to Written Opinion dated May 22, 2015.

* cited by examiner

*Primary Examiner* — Sikarl Witherspoon (57) ABSTRACT

A process of controlling hydroformylation reaction fluid temperature involves controlling the flow rate of reaction fluid through an external heat exchanger.

11 Claims, 3 Drawing Sheets

HYDROFORMYLATION PROCESS

BACKGROUND OF THE INVENTION

The invention relates to a stable hydroformylation process.

It is known that aldehydes can be produced by a continuous process comprising reacting an olefinically unsaturated compound with carbon monoxide and hydrogen in the presence of a metal-organophosphorus ligand complex catalyst. This process is disclosed in, e.g., 'U.S. Pat. No. 4,148,830; U.S. Pat. No. 4,717,775; and U.S. Pat. No. 4,769,498. Reaction temperature is an important hydroformylation process variable for several reasons.

It is generally recognized that steady and controlled operation of a commercial-scale hydroformylation plant is highly desirable. It is also clear that accurate temperature control is critical to catalyst life. The problem of temperature control in hydroformylation reactions on a commercial scale has long been recognized. In section 1.2.4 in J. Falbe (ed) "New Syntheses with Carbon Monoxide" (Springer-Verlag, N Y 1980) a summary of the problem with a diagram of erratic temperature behavior is shown. A more detailed analysis is given in E. P. Van Elk, P. C. Borman, J. A. M. Kuipers, G. F. Versteeg; *Chemical Engineering Science* 56 (2001) 1491-1500) where the complications of stability and dynamic behavior are discussed. Rhodium hydroformylation reactions are characterized by complex kinetics, mass flow issues, and their very exothermic (28-35 kcal (118-147 kJ)/mol olefin) nature, all of which make temperature control quite difficult.

U.S. Pat. No. 4,277,627 teaches several routes of catalyst deactivation including intrinsic deactivation. Operating conditions are specified to minimize the loss of activity with phosphine-based catalysts. Temperature is a key variable that controls the rate of catalyst deactivation.

In addition to its effect on catalyst stability, controlling the temperature can have a significant impact on the efficiency of the process. Lower temperatures give lower reactivity and result in lost olefin through the system. Higher temperatures give higher ligand decomposition and heavies formation rates due to inevitable aldol formation, as taught in U.S. Pat. No. 4,148,830. Other temperature-related effects, such as higher hydrogenation (to alkane or alcohol) and variation of the normal-to-branched ("N:I") product ratio, may also negatively impact plant productivity.

Generally speaking, to control the temperature, one must control the rate of heat generation and/or the rate of heat removal. At steady state, these two are equal. The rate of heat generation generally will be determined by factors such as the desired plant production rate, and the nature of the olefin (ethylene being highly reactive followed by primary then secondary olefins) and catalyst concentration, to name a few. The production rate and olefin used are generally not changed due to the resulting negative impact on plant economics. Therefore, most of the focus has been on heat removal.

The removal of heat from a heat exchanger is traditionally described by the following equation:

$$\text{Heat Removal} = A * U * \Delta T \quad (1)$$

where "U" is a heat transfer coefficient dependant on the conditions on both the process and coolant side of the equipment (viscosity, sensible heat, flow rates, presence of bubbles, etc.), "A" is the surface area available for the heat transfer and $\Delta T$ is the temperature difference between the product fluid and the coolant.

The surface area of the exchanger is generally a constant. Large internal cooling coils inside a reactor take up valuable reactor space, so it is common practice to use external heat exchangers on reactors needing a substantial amount of heat removal. See WO 2012/008717 A2, U.S. Pat. No. 4,523,036, U.S. Pat. No. 8,389,774 and U.S. Pat. No. 5,367,106. Increasing the size of the heat exchanger to have a very large surface area will generally give better stability but is expensive, increases the plant footprint, and increases maintenance costs.

There are disclosures that aim at controlling the reactor temperature via manipulation of operating conditions. For example, with the highly active phosphite-based Rh catalyst systems disclosed in U.S. Pat. No. 5,744,650, optimizing the temperature difference, $\Delta T$, between the process and coolant side of heat exchangers is critical to steady temperature control. That patent gives a good overview of practical heat exchanger design used to control hydroformylation reactors but focuses on the coolant side of the heat exchanger. Unfortunately, controlling the temperature of the cooling water adds complexity and expense to the plant construction and operation. It also adds considerable process control response delay, in that changes to the cooling water temperature take time, and then the altered cooling water has to re-establish a temperature at the heat exchanger, which then must establish a new $\Delta T$ to show an effect at the reactor. The large masses involved in industrial scale hydroformylation processes greatly increase the response time.

Traditionally the other means to effect heat removal is based on changing the coolant mass flow rate in the heat exchanger. Changing the flow on the coolant side has been viewed as the preferred path since the piping and equipment on the coolant side are generally much smaller than the process side, e.g., 6 inch vs. 20 inch pipes, and involve less expensive metals, e.g., carbon steel compared to stainless steel on the process side.

It is also known that reaction kinetics, which are affected by temperature, have a large impact on process stability. U.S. Pat. No. 5,763,679 teaches that deactivation of metal-organophosphorus ligand complex catalysts caused by inhibiting or poisoning phosphorus compounds can be reversed or reduced by conducting the hydroformylation process in a reaction region where the hydroformylation reaction rate is of a negative or inverse order in carbon monoxide. The presence of both positive and negative order kinetics (as well as varying levels of inhibitors) makes controlling these highly active catalysts very challenging using conventional process control strategies.

U.S. Pat. No. 5,362,917 discloses a method of controlling the stability of hydroformylation processes by varying the flow rate of a synthesis feed gas or the flow rate of a vent gas to maintain a predetermined constant carbon monoxide partial pressure in the hydroformylation process. Since the product isomer (N:I) ratio is dependent on the CO partial pressure, attempting to maintain the CO partial pressure may stabilize the N:I ratio but not the reaction rate at the same time, since the other reagents may be changing as well. Additionally, using one reagent out of three to control the reactivity is limited by the amount of inventory of reagent already in the reactor.

Similarly, U.S. Pat. No. 7,446,231 deals with controlling the reaction by manipulating the reactor total pressure. This attempts to deal simultaneously with several gaseous reagents that impact the kinetics. Instead of setting a fixed CO partial pressure, the total pressure is maintained at a constant propylene feed rate based on the observation that the CO and $H_2$ partial pressure will self-control, and the hope that a steadier process will result. As shown in FIG. 1 in U.S. Pat. No. 7,446,231, the optimal operating region is at the peak of the hydroformylation rate versus CO partial pressure plot, where the highest rate and N:I performance is observed. Unfortunately, operating at this peak is inherently unstable since kinetic models do not account for changing reaction orders (including zero order at the peak itself). Therefore, the technique of U.S. Pat. No. 7,446,231 only applies in the negative order region.

Figure 1:
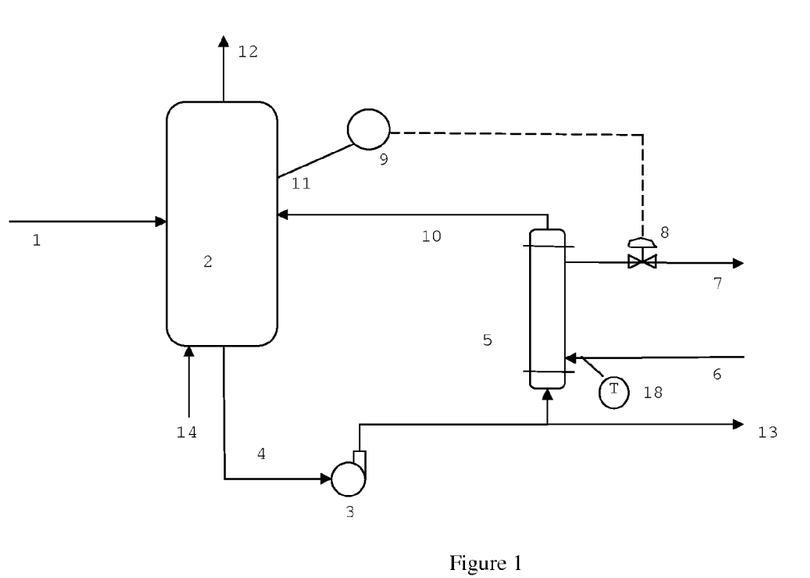
FIG. 1 is a schematic of a prior art hydroformylation process.

Thus, hydroformylation reactors typically operate in an inherently unstable regime and depend on the reactor control system to maintain stable process control. Conventional hydroformylation reactor temperature control systems have adjusted the cooling water inlet temperature, cooling water flow rate, or a combination of these to control the reactor liquid temperature. FIG. 1 depicts a conventional hydroformylation process. Conventional hydroformylation reactor temperature control systems that adjust the cooling water inlet temperature, as measured by temperature sensor (18), the flow rate of cooling water outlet stream (7), or a combination thereof in order to control the reactor liquid temperature. Hydroformylation reactor liquid temperature, as measured by temperature sensor (11), is compared to the set point by controller (9) for temperature control of the process, and is maintained at a desired steady value. Historically, this control scheme has worked reasonably well, primarily because the first generation, commercial hydroformylation catalysts had relatively low reaction rates, e.g., less than 2 gmoles aldehyde/liter reactor volume/hr, which generated relatively low reaction heat per unit time/volume. However, recently commercialized next-generation hydroformylation catalysts have significantly higher reaction rates compared to prior catalysts. The higher reaction rates result in higher heat generation in the hydroformylation reactor per unit time. The conventional reactor temperature control scheme is too slow for effective reactor temperature control of reactions that use the new hydroformylation catalysts.

In view of the shortcomings of the prior art, it would be desirable to have an improved reactor temperature control process for hydroformylation reactors.

SUMMARY OF THE INVENTION

The process of the invention is such a process, comprising contacting CO, $H_2$, and at least one olefin in the presence of a hydroformylation catalyst in a reaction fluid in at least one reactor under hydroformylation conditions sufficient to form at least one aldehyde product,
removing a stream of the reaction fluid from the at least one reactor and passing the stream to a heat exchanger,
removing a quantity of heat from the stream to form a cooled stream, and
returning the cooled stream to the reactor,
wherein the flow rate of at least a portion of at least one of the stream and/or the cooled stream is controlled in order to control the temperature in the reactor.

Surprisingly, the process of the invention provides fast response times and good control of hydroformylation reactor temperature.

DETAILED DESCRIPTION OF THE INVENTION

This invention pertains to a method of stabilizing a hydroformylation process against rapid, often extreme, change or cycling of reaction rate and/or process parameters, such as temperature. The process of the invention is a continuous one for producing aldehydes by the hydroformylation of alpha-olefins. Aldehydes produced by such processes have a wide range of utility, for example, as intermediates for hydrogenation to aliphatic alcohols, for amination to aliphatic amines, for oxidation to aliphatic acids, and for aldol condensation to produce plasticizers.

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but not limited to, all permissible asymmetric and non-asymmetric hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds formed in the reaction (which may be homogeneous or heterogeneous, and these compounds include those adhered to process equipment surfaces). The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous buffer solution, (g) a treated fluid returned to a reaction zone or separation zone, (h) a fluid in an external cooler, and (i) ligand decomposition products and their salts.

"Hydrolyzable organophosphorous ligands" are trivalent phosphorous ligands that contain at least one P—Z bond wherein Z is oxygen, nitrogen, chlorine, fluorine or bromine Examples include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligands may include chelate structures and/or may contain multiple P—Z moieties such as polyphosphites, polyphosphoramidites, etc. and mixed P—Z moieties such as phosphite-phosphoramidites, flurophosphite-phosphites, and the like.

The term "complex" as used herein means a coordination compound formed by the union of one or more electronically rich molecules or atoms (i.e., ligand) with one or more electronically poor molecules or atoms (i.e., transition metal). For example, the organophosphorous ligand employable herein possesses one phosphorus (III) donor atom having one unshared pair of electrons, which is capable of forming a coordinate covalent bond with the metal. A polyorganophosphorous ligand employable herein possesses two or more phosphorus (III) donor atoms, each having one unshared pair of electrons, each of which is capable of forming a coordinate covalent bond independently or possibly in concert (for example, via chelation) with the transition metal. Carbon monoxide can also be present and complexed with the transition metal. The ultimate composition of the complex catalyst may also contain an additional ligand(s) such as described above, for example, hydrogen, mono-olefin, or an anion satisfying the coordination sites or nuclear charge of the metal.

The number of available coordination sites on the transition metal is well known in the art and depends upon the particular transition metal selected. The catalytic species may comprise a complex catalyst mixture of monomeric, dimeric or higher nuclearity forms, which forms preferably are characterized by at least one organophosphorus-containing molecule complexed per one molecule of metal, for example, rhodium. For instance, it is considered that the catalytic species of the preferred catalyst employed in the hydroformylation reaction may be complexed with carbon monoxide and hydrogen in addition to one or more organophosphorous ligand(s).

The disclosed process comprises contacting CO, $H_2$, and at least one olefin under hydroformylation conditions sufficient to form at least one aldehyde product in the presence of a hydroformylation catalyst comprising, as components, a transition metal and an organophosphorous ligand. Optional process components include an amine and/or water such as described in U.S. Pat. No. 5,288,918, U.S. Pat. No. 5,731,472, and U.S. Pat. No. 5,741,944.

Hydrogen and carbon monoxide may be obtained from any suitable source, including petroleum cracking and refinery operations. Syngas mixtures are a preferred source of hydrogen and CO.

Syngas (from synthesis gas) is the name given to a gas mixture that contains varying amounts of CO and $H_2$. Production methods are well known. Hydrogen and CO typically are the main components of syngas, but syngas may contain $CO_2$ and inert gases such as $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO ratio is between 3:1 and 1:3 and more preferably is from about 1:2 to 2:1.

The substituted or unsubstituted olefinic unsaturated reactants that may be employed in the hydroformylation process include both optically active (prochiral and chiral) and non-optically active (achiral) olefinic unsaturated compounds containing from 2 to 40, preferably 3 to 20, carbon atoms. These compounds are described in detail in US 2010/006980. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403).

Prochiral and chiral olefins useful in the asymmetric hydroformylation that can be employed to produce enantiomeric aldehyde mixtures include those represented by the formula:

wherein $R^1$, $R^2$, $R^3$ and $R^4$ are the same or different (provided that $R^1$ is different from $R^2$ or $R^3$ is different from $R^4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, and carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation are described, for example, in U.S. Pat. Nos. 4,329,507, 5,360,938 and 5,491,266.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit Illustrative preferred solvents include ketones (e.g., acetone and methylethyl ketone), esters (e.g., ethyl acetate, di-2-ethylhexyl phthalate, 2,2,4-trimethyl-1,3-pentanediol monoisobutyrate), hydrocarbons (e.g., toluene), nitrohydrocarbons (e.g., nitrobenzene), ethers (e.g., tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. No. 4,148,380 and U.S. Pat. No. 4,247,486. The primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

Illustrative metal-organophosphorous ligand complexes employable in such hydroformylation reactions include metal-organophosphorous ligand complex catalysts. These catalysts, as well as methods for their preparation, are well known in the art and include those disclosed in the patents mentioned herein. In general, such catalysts may be preformed or formed in situ and comprise metal in complex combination with an organophosphorous ligand, carbon monoxide and optionally hydrogen. The ligand complex species may be present in mononuclear, dinuclear and/or higher nuclearity forms. However, the exact structure of the catalyst is not known.

The metal-organophosphorous ligand complex catalyst can be optically active or non-optically active. The metals can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Mixtures of these metals may be used. The permissible organophosphorous ligands that make up the metal-organophosphorous ligand complexes and free organophosphorous ligand include mono-, di-, tri- and higher polyorganophosphorus ligands. Mixtures of ligands may be employed in the metal-organophosphorous ligand complex catalyst and/or free ligand, and such mixtures may be the same or different.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Among the organophosphorous ligands that may serve as the ligand of the metal-organophosphorous ligand complex catalyst are triarylphosphines, monoorganophosphite, diorganophosphite, triorganophosphite, organopolyphosphite, organomonophosphoramidite and organopolyphosphoramidite compounds and other hydrolyzable organophosphorous compounds. Such organophosphorous ligands and methods for their preparation are well known in the art.

The triarylphosphine employable in the process of this disclosure comprises any organic compound comprising one phosphorus atom covalently bonded to three aryl or arylalkyl radicals, or combinations thereof. A mixture of triarylphosphine ligands may also be employed. Representative organomonophosphines include those having the formula:

(I)

wherein each $R^{29}$, $R^{30}$ and $R^{31}$ may be the same or different and represent a substituted or unsubstituted aryl radical containing from 4 to 40 carbon atoms or greater. Such triarylphosphines may be found described in greater detail, for example, in U.S. Pat. No. 3,527,809, the disclosure of which is incorporated herein by reference. Illustrative triarylphosphine ligands are triphenylphosphine, trinaphthylphine, tritolylphosphine, tri(p-biphenyl)phosphine, tri(p-methoxyphenyl) phosphine, tri(m-chlorophenyl)-phosphine, p-N,N-dimethylaminophenyl bis-phenyl phosphine, and the like. Triphenyl phosphine, i.e., the compound of Formula I wherein each $R^{29}$, $R^{30}$ and $R^{31}$ is phenyl, is an example of a preferred organomonophosphine ligand. The hydroformylation reaction is preferentially effected in a liquid body containing excess, free triarylphosphine.

Representative monoorganophosphites, diorganophosphites, triorganophosphites, and organopolyphosphites (containing two or more tertiary (trivalent) phosphorus atoms) may include those having the following formulae that are described in detail in WO/2012/14541:

As a further option, any organophosphoramidite ligand can be used as the, or in combination with any other, organophosphorous ligand, and any organopolyphosphoramidite ligand can be used as the, or in combination with any other, organophosphorous ligand. Organophosphoramidite ligands are known, and they are used in the same manner as organophosphite ligands. Representative organophosphoramidite ligands are of formulae (X-XII).

Organophosphoramidites are further described in, for example, U.S. Pat. No. 7,615,645. As here used "organophosphorous ligands" and like terms include organomonophosphoramidite and organopolyphosphoramidite ligands unless specifically noted otherwise.

Specific illustrative examples of such organophosphorous ligands include the following: 2-t-butyl-4-methoxyphenyl(3,3'-di-t-butyl-5,5'-dimethoxy-1,1'-biphenyl-2,2'-diyl)phosphite, methyl(3,3'-di-t-butyl-5,5'-dimethoxy-1,1'-biphenyl-2,2'-diyl)phosphite, 6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin, 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin, (2R,4R)-di[2,2'-(3,3',5,5'-tetrakis-tert-butyl-1,1-biphenyl)]-2,4-pentyldiphosphite, (2R,4R)di[2,2'-(3,3'-di-tert-butyl-5,5'-dimethoxy-1,1'-biphenyl)]-2,4-pentyldiphosphite, 2-[[2-[[4,8,-bis(1,1-dimethylethyl), 2,10-dimethoxydibenzo-[d,f][1,3,2]dioxophosphepin-6-yl]oxy]-3-(1,1-dimethylethyl)-5-methoxyphenyl]methyl]-4-methoxy, methylenedi-2,1-phenylene tetrakis[2,4-bis(1,1-dimethylethyl)phenyl]ester of phosphorous acid, and [1,1'-biphenyl]-2,2'-diyl tetrakis [2-(1,1-dimethylethyl)-4-methoxyphenyl]ester of phosphorous acid.

The metal-organophosphorous ligand complex catalysts may be in homogeneous or heterogeneous form. For instance, preformed rhodium hydrido-carbonyl-organophosphorous ligand catalysts may be prepared and introduced into a hydroformylation reaction mixture. More preferably, the rhodium-organophosphorous ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$, and the like may be introduced into the reaction mixture along with the organophosphorous ligand for the in situ formation of the active catalyst. In a preferred embodiment, rhodium dicarbonyl acetylacetonate is employed as a rhodium precursor and reacted in the presence of a solvent with the organophosphorous ligand to form a catalytic rhodium-organophosphorous ligand complex precursor that is introduced into the reactor along with excess (free) organophosphorous ligand for the in situ formation of the active catalyst. In any event, it is sufficient that carbon monoxide, hydrogen and the organophosphorous ligand are all ligands that are capable of being complexed with the metal and that an active metal-organophosphorous ligand catalyst is present in the reaction mixture under the conditions used in the hydroformylation reaction. Carbonyl and organophosphorous ligands may be complexed to the rhodium either prior to or in situ during the hydroformylation process.

By way of illustration, a preferred catalyst precursor composition consists essentially of a solubilized rhodium carbonyl organophosphorous ligand complex precursor, a solvent and, optionally, free organophosphorous ligand. The preferred catalyst precursor composition can be prepared by forming a solution of rhodium dicarbonyl acetylacetonate, an organic solvent and a organophosphorous ligand. The organophosphorous ligand readily replaces one of the carbonyl ligands of the rhodium acetylacetonate complex precursor as witnessed by the evolution of carbon monoxide gas.

Accordingly, the metal-organophosphorus ligand complex catalyst advantageously comprise the metal complexed with carbon monoxide and an organophosphorous ligand, said ligand being bonded (complexed) to the metal in a chelated and/or non-chelated fashion.

Mixtures of catalysts can be employed. The amount of metal-organophosphorous ligand complex catalyst present in the reaction fluid need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal.

In addition to the metal-organophosphorous ligand complex catalyst, free organophosphorous ligand (i.e., ligand that is not complexed with the metal) may also be present in the reaction medium. The free organophosphorous ligand may correspond to any of the above-defined organophosphorous ligands discussed above. It is preferred that the free organophosphorous ligand be the same as the organophosphorous ligand of the metal-organophosphorous ligand complex catalyst employed. However, such ligands need not be the same in any given process. The hydroformylation process of this invention may involve from 0.1 moles or less to 100 moles or higher of free organophosphorous ligand per mole of metal in the reaction medium. Preferably, the hydroformylation process is carried out in the presence of from 1 to 50 moles of free organophosphorous ligand per mole of metal present in the reaction medium. More preferably, for organopolyphosphites, from 0.1 to 4 moles of free organopolyphosphite ligand are employed per mole of metal. If desired, additional organophosphorous ligand can be supplied to the reaction medium of the hydroformylation process at any time and in any suitable manner, e.g., to maintain a predetermined level of free ligand in the reaction medium.

The hydroformylation process is well known and widely commercially practiced. See, e.g., U.S. Pat. Nos. 4,148,830, 5,237,106, 5,763,679, 5,741,945, 5,767,321, 7,446,231, 7,906,688, and 7,863,487. The reaction conditions of the hydroformylation processes may include any suitable type hydroformylation conditions heretofore employed for producing optically active and/or non-optically active aldehydes. The hydroformylation reaction conditions employed will be governed by the type of aldehyde product desired. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominately by the amount of reactants necessary to obtain a desired rate of reaction. More specifically, the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, the molar ratio of gaseous $H_2$:CO may range from 1:10 to 100:1 or higher, the more preferred molar ratio being from 1:10 to 10:1. In general, the hydroformylation process may be conducted at any operable reaction temperature. Advantageously, the hydroformylation process is conducted at a reaction temperature from $-25°$ C. to $200°$ C., preferably from $50°$ C. to $120°$ C. Advantageously, the reaction temperature is less than $100°$ C. in the reactor being cooled by the process of the invention.

The newer "next-generation" hydroformylation catalysts (typically based on hydrolyzable organophosphorus ligands) have a higher reaction rate, e.g., greater than 2 gmoles aldehyde/liter reactor volume/hour, compared to older catalysts. The reaction rates also exhibit complex kinetics (e.g., positive and negative reaction orders with respect to CO). These catalysts typically operate at lower reaction temperatures, e.g., 60 to $80°$ C., in order to minimize catalyst degradation. The lower operating temperatures result in a lower $\Delta T$ between cooling medium and reaction medium, thus reducing heat exchanger heat removal capability. These factors have made designing adequate temperature control systems more complicated than for prior art processes.

It has been found that an improved hydroformylation reaction temperature control method involves designing the temperature control scheme around controlling the temperature of the reactor contents by controlling aspects of a stream that circulates from the reactor through an external heat exchanger and back to the reactor. As mentioned hereinabove, prior art control schemes focused on the coolant side of the external heat exchanger. The process of the invention controls aspects of the process side of the external heat exchanger. In one embodiment of the invention, the process of the invention controls the steady state reaction temperature within $+/-1°$ C. of the set point, preferably within $+/-0.5°$ C. of the set point.

It should be understood that the nature of the catalyst is not critical to the invention. It is preferred that the catalyst exhibit high reactivity (greater than 2 gmoles aldehyde/liter reactor volume/hour in the reactor).

When more than one hydroformylation reactor is used for a given olefin, the hydroformylation reactors downstream of the first reactor in a train may operate at higher temperatures, but since the amount of available olefin has been greatly reduced by the time the reaction fluid reaches the downstream reactors, the amount of heat being generated even at these elevated temperatures is low enough that conventional cooling schemes can be employed for the downstream reactors. In one embodiment of the invention, the cooling scheme of the invention is used for all reactors. However, any combination of control schemes is possible.

Figure 2:
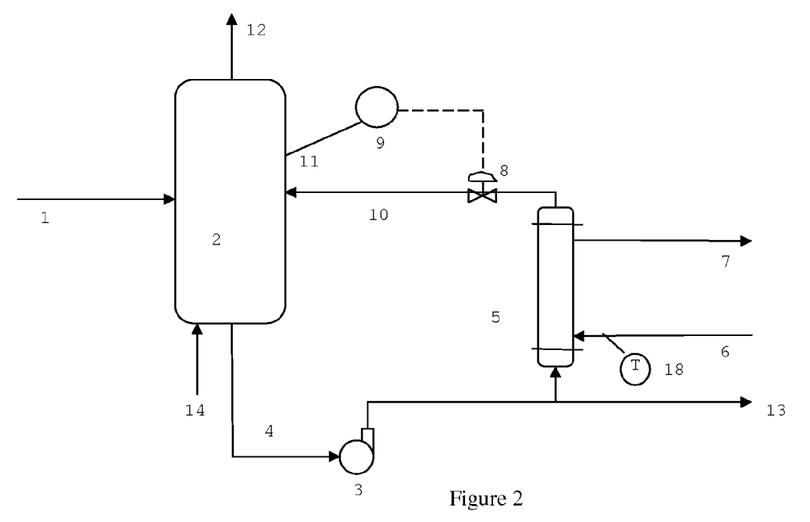
FIG. 2 is a schematic of an exemplary process of the invention.

In one embodiment of the invention, with reference to FIG. 2, the temperature of the reaction fluid in the reactor (2), or in a pipe (4) exiting the reactor, is measured using a temperature sensing device (11). A signal indicating the value of the temperature measurement is sent from the sensing device to a temperature controller device (9). A signal from the temperature controller (9) is sent to control valve (8) in order to control the flow rate of the stream (10) that is circulated from the reactor (2) to the external heat exchanger (5) and then back to the reactor (2) by means of pump (3) and the related piping (4) and (10). In this embodiment, it is preferred to set the flow rate and temperature of the cooling water stream (6), measured at cooling water inlet (18) at constant values.

Figure 3:
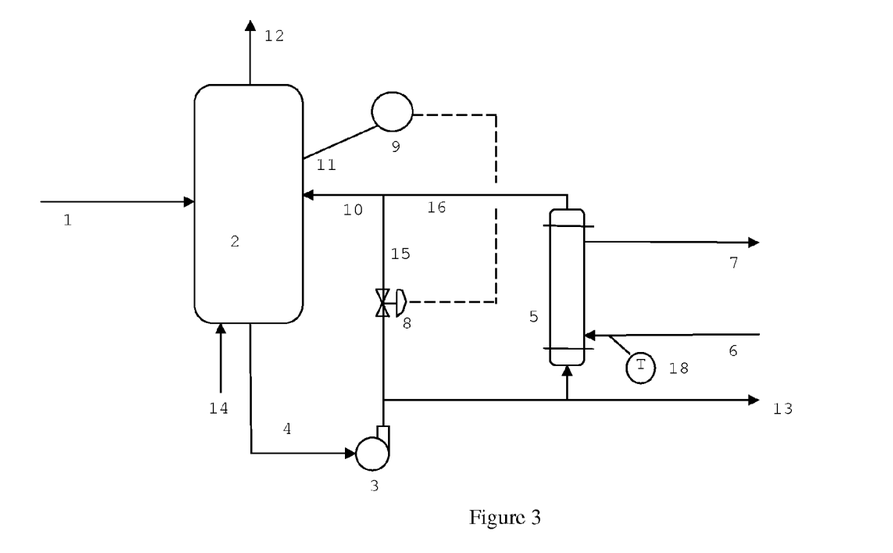
FIG. 3 is a schematic of an exemplary process of the invention.

Another embodiment is shown in FIG. 3 wherein a by-pass line (15) around the external cooler (5) is present, and thus changes in the flow rate of the by-pass stream change the temperature of stream (10) quickly and maintain an essentially constant total flow in stream (10) back to the reactor. The temperature of stream (10) is determined by the ratio of the flow rates of streams (15) and (16). This rapid control of the temperature in stream (10), and thus the amount of heat removal from reactor (2), allows for rapid response to temperature changes in the reactor.

Another embodiment employs a by-pass line that goes from the pump discharge line through a flow resistance device (typically an orifice plate, but any other flow resistance device would be acceptable), and back to the suction or inlet line of the pump to give rapid and reversible control of fluid flow through the heat exchanger. The valve (8) is preferably located on the discharge side of the pump before the heat exchanger but can alternatively be located after the heat exchanger.

In one embodiment of the invention, pump (3) is a variable speed pump to vary the amount of flow through the heat exchanger. However, those skilled in the art will be able to employ any suitable pump.

It is to be understood than any combination of the above embodiments can be used.

The process can be implemented using process control hardware and software that are readily commercially available, as is known to those skilled in the art. The improved reactor control and stability of the process of the invention provides a useful basis for the effective implementation of Advanced Process Control (APC) strategies such as Multi-variable Model Predictive Control (MMPC), Dynamic Matrix Control (DMC), Real Time Optimization (RTO) or Advanced Control and Optimization (AC&O).

Any suitable process equipment can be employed. The design and construction, including selection of suitable materials of construction, of hydroformylation process equipment is well known to those skilled in the art. In one embodiment of the invention, the heat exchanger is capable of removing at least 75 kW/m$^3$ of reactor volume from the stream.

In the embodiment shown in FIG. 2, one external heat exchanger is employed. It is also possible to employ different configurations of cooling equipment. For example, any combination of cooling coils, reactor jacket cooling, and external heat exchange can be employed. It is preferred to employ at least one external heat exchanger.

Compared to prior art processes, the process of the invention may provide a more rapid response to temperature changes. Compared to the prior art, if an increased reactor temperature is detected, increasing the flow of cooled process fluid to the reactor rapidly delivers cooling to the reactor, reducing its temperature. The heat exchanger will experience increased demand in such situations, and temperatures within the heat exchanger may fluctuate, but such temperature fluctuation in the heat exchanger is preferred over fluctuation in the reactor.

SPECIFIC EMBODIMENTS OF THE INVENTION

The following examples are given to illustrate the invention and should not be construed as limiting its scope.

Comparative Experiment A (Not an Embodiment of the Invention)

To illustrate the operation of the conventional hydroformylation reactor control scheme, a simulation is conducted. The process flow shown in FIG. 1 is the basis for this simulation. The hydroformylation reactor (2), pump, (3), and external cooler, (5) from FIG. 1 are modeled using Aspen Plus Dynamics™ software, which is commercially available. Typical initial process conditions used in the model are given below:

Process flow to heat exchanger=1,816 metric tons/hour
Process flow temperature=95° C.
Cooling Water Flow=735 metric tons/hr
Cooling Water Inlet Temperature=48° C.
Cooling Water Outlet Temperature=73° C.
Heat Exchanger Heat Load=21,600 KW
Heat Exchanger Area=1160 square meters
Heat Exchanger Heat Transfer Coefficient=0.85 kW/square meter/K
Reactor Reaction Rate=5.6 gmoles/liter/hr.

Figure 4:
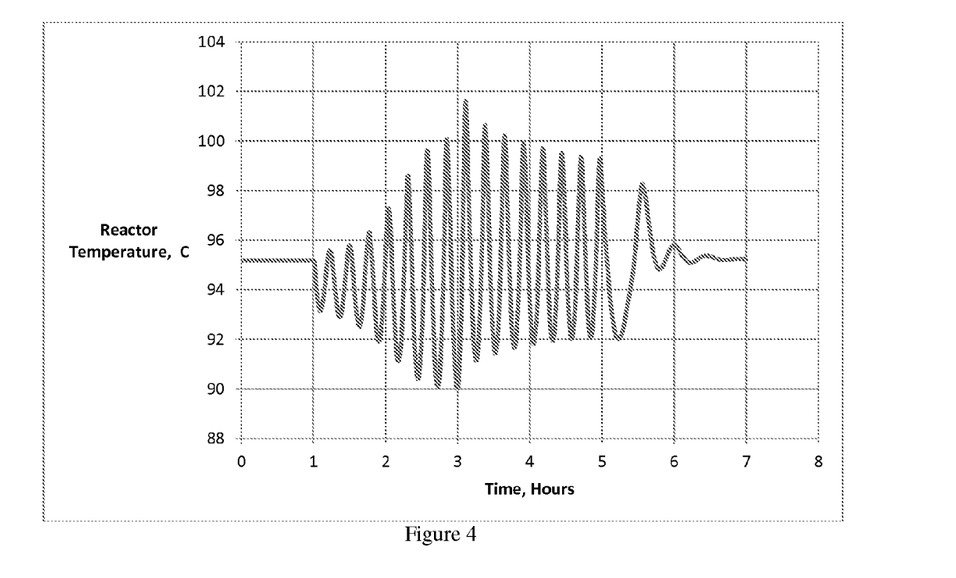
FIG. 4 is a graph of the results of Comparative Experiment A.

The results of the conventional reactor temperature control scheme are shown in FIG. 4. The simulation begins with a steady state reactor temperature of 95° C. After one hour, the reactor temperature controller set point is lowered by 1° C. This temperature set point change initiates an oscillating, unstable reactor temperature that is a result of the process control dynamics of the system. After 5 hours, the reactor temperature control set point is raised back to the original set point. Over the next 2 hours, the reactor temperature returns to the original steady state value.

Example 1

Figure 5:
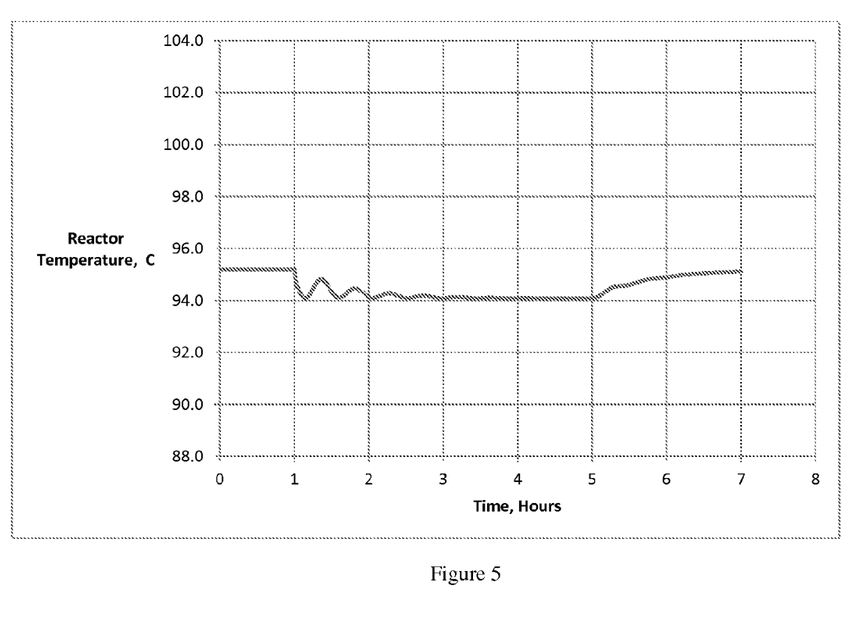
FIG. 5 is a graph of the results of Example 1.

Comparative Experiment A is repeated except that the process shown in FIG. 2 is used as the basis of the simulation, to allow the reactor temperature controller (9) to adjust the flow rate of process fluid liquid circulation through the external cooler, (5) using valve (8) now located on line (10). The other difference is that the Cooling Water Inlet Temperature is fixed at 48° C., as opposed to being controlled. The results of the improved reactor temperature control scheme are shown in FIG. 5. The simulation begins with a steady state reactor temperature of 95° C. After one hour, the reactor temperature controller set point is lowered by 1° C. This temperature set point change does not initiate the high amplitude oscillating, unstable reactor temperature of the conventional control system. Instead, the reactor temperature control response is very stable and controlled for hours 1 to 5.

At hour 5, the reactor temperature control set point is increased to 95° C. The reactor temperature returns to the original temperature within 2 hours.

The data from Ex. 1 and C. E. A demonstrate that the process of the invention can achieve dramatic improvement in the control of hydroformylation reactions. Controlling the flow of stream (10) results in a more robust, stable reactor temperature control system while providing a wider operating window of stable operation for the hydroformylation reactor. The response time for this scheme has been found to be much faster than the prior art designs, and provides surprisingly improved control of reactor temperature.

What is claimed is:

1. A process comprising
    contacting CO, $H_2$, and at least one olefin in the presence of a hydroformylation catalyst in a reaction fluid in at least one reactor under hydroformylation conditions sufficient to form at least one aldehyde product,
    removing a stream of the reaction fluid from the at least one reactor and passing the stream to a heat exchanger,
    removing a quantity of heat from the stream to form a cooled stream, and
    returning the cooled stream to the reactor,
    wherein the flow rate of at least a portion of at least one of the stream and/or the cooled stream is controlled in order to control the temperature in the reactor, and
    wherein the steady state reaction temperature is controlled within +/−1° C. of the set point.

2. The process of claim 1 wherein the reaction rate is greater than 2 gmoles aldehyde/liter reactor volume/hour.

3. The process of claim 1 wherein the catalyst comprises a hydrolyzable organophosphorus ligand.

4. The process of claim 1 wherein the catalytic metal of the catalyst is rhodium.

5. The process of claim 1 wherein the reaction temperature is less than 100° C.

6. The process of claim 1 wherein the heat exchanger is capable of removing at least 75 kW/m$^3$ of reactor volume from the stream.

7. The process of claim 1 wherein the steady state reaction temperature is controlled within +/−0.5° C. of the set point.

8. The process of claim 1 wherein the flow rate of at least a portion of the cooled stream is controlled in order to control the temperature in the reactor.

9. The process of claim 1 wherein the flow rate of at least a portion of the stream is controlled in order to control the temperature in the reactor.

10. The process of claim 1 wherein at least one Advanced Process Control (APC) strategy is employed to control the hydroformylation process.

11. A process comprising
    contacting CO, $H_2$, and at least one olefin in the presence of a hydroformylation catalyst in a reaction fluid in at least one reactor under hydroformylation conditions sufficient to form at least one aldehyde product,
    removing a stream of the reaction fluid from the at least one reactor and passing the stream to a heat exchanger,
    removing a quantity of heat from the stream to form a cooled stream, and
    returning the cooled stream to the reactor,
    wherein the flow rate of at least a portion of at least one of the stream and/or the cooled stream is controlled in order to control the temperature in the reactor, wherein the steady state reaction temperature is controlled within +/−1° C. of the set point, wherein the reaction rate is greater than 2 gmoles aldehyde/liter reactor volume/hour, and wherein the reaction temperature is less than 100° C.

* * * * *